United States Patent [19]
Kumar

[11] Patent Number: 6,117,451
[45] Date of Patent: Sep. 12, 2000

[54] DIRECT COMPRESSION METFORMIN HYDROCHLORIDE TABLETS

[75] Inventor: Vijai Kumar, Morris Plains, N.J.

[73] Assignee: Pharmalogix, Inc., Denville, N.J.

[21] Appl. No.: 09/139,361

[22] Filed: Aug. 25, 1998

[51] Int. Cl.[7] ................................ A61K 9/20; A61K 9/22
[52] U.S. Cl. .................... 424/465; 424/464; 424/468; 424/489; 514/770; 514/772.3; 514/777; 514/781; 514/784; 514/951; 514/960
[58] Field of Search ..................... 424/464, 465, 424/489, 468, 469, 470

[56] References Cited

U.S. PATENT DOCUMENTS 5,955,106  9/1999  Moeckel et al. .................. 424/464

*Primary Examiner*—James M. Spear
*Attorney, Agent, or Firm*—Herbert Dubno

[57] ABSTRACT

Metformin Hydrochloride (herein referred to as metformin HCl) that may be 98.5%–100% pure is a high dose drug capable of being directly compressed with specific excipients into tablets having desired, hardness, disintegrating ability, and acceptable dissolution characteristics. Metformin HCl is not inherently compressible and thus presents formulation problems. Excipients used in the formulation enhance the flow and compaction properties of the drug and tableting mix. Optimal flow contributes to uniform die fill and weight control. The binder used ensures sufficient cohesive properties that allow metformin HCl to be compressed using the direct compression method. The tablets produced provide an acceptable in-vitro dissolution profile.

9 Claims, No Drawings

DIRECT COMPRESSION METFORMIN HYDROCHLORIDE TABLETS

FIELD OF THE INVENTION

This invention relates to new direct compression metformin hydrochloride tablets, a process for the preparation thereof, and to new metformin hydrochloride formulations in the form of a tableting powder, capable of being directly compressed into the metformin hydrochloride tablets. The invention relates further to a process for preparing the direct compression metformin hydrochloride tablets by blending metformin and specific excipients into the new metformin hydrochloride formulations and then directly compressing the formulations into the direct compression tablets.

BACKGROUND OF THE INVENTION

Metformin HCl is hygroscopic, presents stability problems, and is not inherently compressible. Consequently, there is a need to provide a free-flowing and cohesive metformin HCl composition capable of being directly compressed into strong tablets with an acceptable in vitro dissolution profile.

Tablets may be defined as solid dosage pharmaceutical forms containing drug substances with or without suitable fillers. They are produced by compression or compaction of a formulation containing the drug and certain excipients selected to aid in the processing and to improve the properties of the product. Tablets may be coated or uncoated and are made from powdered, crystalline materials. They may include various diluents, binders, disintegrants, lubricants, glidants and in many cases, colorants. Excipients used are classified according to the function they perform. For example, a glidant may be used to improve the flow of powder blend in the hopper and into the tablet die.

There has been widespread use of tablets since the latter part of the $19^{th}$ century and the majority of pharmaceutical dosage forms are marketed as tablets. Major reasons of tablet popularity as a dosage form among pharmaceutical manufacturers are simplicity, low cost, and the speed of production. Other reasons include stability of drug product, convenience in packaging, shipping, and dispensing. To the patient or consumer, tablets offer convenience of administration, ease of accurate dosage, compactness, portability, blandness of taste, ease of administration, and elegant distinctive appearance.

Tablets may be plain, film or sugar coated, bisected, embossed, layered, or sustained release. They can be made in a variety of sizes, shapes and colors. Tablets may be swallowed, chewed, or dissolved in the buccal cavity or beneath the tongue. They may be dissolved in water for local or topical application. Sterile tablets are normally used for parenteral solutions and for implantation beneath the skin.

In addition to the active or therapeutic ingredients, tablets may contain a number of inert materials known as excipients. They may be classified according to the role they play in the final tablet. The primary composition includes a filler, binder, lubricant, and glidant. Other excipients which give physical characteristics to the finished tablet are coloring agents, and flavors in the case of chewable tablets. Without excipients most drugs and pharmaceutical ingredients cannot be directly compressed into tablets. This is primarily due to the poor flow and cohesive properties of most drugs. Typically, excipients are added to a formulation to impart good flow and compression characteristics to the material being compressed. Such properties are imparted to these excipients through pretreatment steps such as wet granulation, slugging, spray drying spheronization, or crystallization.

Lubricants are typically added to prevent the tableting materials from sticking to punches, minimize friction during tablet compression, and allow for removal of the compressed tablet from the die. Such lubricants are commonly included in the final tablet mix in amounts usually less than 1% by weight.

In addition, tablets often contain diluents which are added to increase the bulk weight of the blend resulting in a practical size for compression. This is often necessary where the dose of the drug is relatively small.

Another commonly used class of excipients in tablets is binders. Binders are agents, which impart cohesive qualities to the powdered material. Commonly used binders include starch, and sugars such as sucrose, glucose, dextrose, and lactose.

Disintegrants are often included to ensure that the tablet has an acceptable rate of disintegration. Typical disintegrants include starch derivatives and salts of carboxymethylcellulose.

Other desirable characteristics of excipients include the following:

High compressibility to allow strong tablets to be made at low compression forces.

Good flow properties that can improve the flow of other excipients in the formula.

Cohesiveness (to prevent tablet from crumbling during processing, shipping and handling).

The three processes for making compressed tablets are wet granulation, direct compression, and dry granulation (slugging or roller compaction). The method of preparation and type of excipients are selected to give the tablet formulation the desired physical characteristics that allow for the rapid compression of the tablets. After compression, the tablets must have a number of additional attributes such as appearance, hardness, disintegrating ability, and an acceptable dissolution profile. Choice of fillers and other excipients will depend on the chemical and physical properties of the drug, behavior of the mixture during processing, and the properties of the final tablets. Preformulation studies are done to determine the chemical and physical compatibility of the active component with proposed excipients.

The properties of the drug, its dosage forms, and the economics of the operation will determine selection of the best process for tableting. Generally, both wet granulation and direct compression are used in developing a tablet.

The dry granulation method may be used where one of the constituents, either the drug or the diluent, has sufficient cohesive properties to be tableted. The method consists of blending, slugging the ingredients, dry screening, lubrication, and compression.

The wet granulation method is used to convert a powder mixture into granules having suitable flow and cohesive properties for tableting. The procedure consists of mixing the powders in a suitable blender followed by adding the granulating solution under shear to the mixed powders to obtain a granulation. The damp mass is then screened through a suitable screen and dried by tray drying or fluidized bed drying. Alternately, the wet mass may be dried and passed through a mill. The overall process includes: weighing, dry powder blending, wet granulating, drying, milling, blending lubrication and compression.

In general, powders do not have sufficient adhesive or cohesive properties to form hard, strong granules. A binder is usually required to bond the powder particles together due to the poor cohesive properties of most powders. Heat and moisture sensitive drugs cannot usually be manufactured using wet granulation. The large number of processing steps and processing time are problems due to high level manufacturing costs. Wet granulation has also been known to reduce the compressibility of some pharmaceutical excipients such as microcrystalline cellulose.

Direct compression is regarded as a relatively quick process where the powdered materials are compressed directly without changing the physical and chemical properties of the drug. The active ingredient(s), direct compression excipients and other auxiliary substances, such as a glidant and lubricant are blended in a twin shell blender or similar low shear apparatus before being compressed into tablets. This type of mixing was believed to be essential in order to prepare "pharmaceutically acceptable" dosage forms. For example, Remington's Pharmaceutical Sciences (RPS), pp 1203 to 1932 17$^{th}$ edition (1985), cautions pharmaceutical scientists that the manner in which a lubricant is added to a formulation must be carefully controlled. Accordingly, lubricants are usually added to a granulation by gentle mixing. RPS warns that prolonged blending of a lubricant with a granulation can materially affect hardness and disintegration time for the resulting tablets. Furthermore, Ansel et al (1995) Pharmaceutical Dosage Forms and Drug Delivery Systems, 6$^{th}$ Ed. p. 199, indicates that excessive blending of lubricants with the granulate ingredients cause water proofing of the granule and reduces tablet hardness or strength of the compressed tablet. For these reasons, high shear mixing conditions have not been used to prepare direct compression dosage forms.

The advantages of direct compression include uniformity of blend, few manufacturing steps involved, (i.e. the overall process involves weighing of powders, blending and compression, hence less cost), elimination of heat and moisture, prime particle dissociation, and physical stability.

Pharmaceutical manufacturers would prefer to use direct compression techniques over wet or dry granulation methods because of quick processing time and cost advantages. However, direct compression is usually limited to those situations where the drug or active ingredient has a crystalline structure and physical characteristics required to form pharmaceutically acceptable tablets. However, one or more excipients must often be combined with the active ingredient before the direct compression method can be used since many ingredients do not have the necessary properties. Since each excipient added to the formulation increases the tablet size of the final product, manufacturers are often limited to using the direct compression method in formulations containing a low dose of the active ingredient per compressed tablet.

A solid dosage form containing a high dose drug (i.e. the drug itself comprises a substantial portion of the total compressed tablet weight) could only be directly compressed if the drug itself has sufficient physical characteristics (e.g. cohesiveness) for the ingredients to be directly compressed.

For an example, metformin HCl (an oral hypoglycemic) is considered a high dose drug. Most tablet formulations include a range of 70 to 85% by weight of metformin HCl per tablet. This high dose drug, combined with its rather poor physical characteristics for direct compression, has not allowed pharmaceutical manufacturers to use direct compression as a method to prepare the final tablet.

For example, in U.S. Pat. No. 5,733,578 on acetaminophen to Hunter et al, acetaminophen could not be directly compressed with microcrystalline cellulose to form acceptable tablets. The final product tended to be soft, prone to capping and otherwise not pharmaceutically acceptable (i.e. difficult to swallow because of the large size). Consequently, the more time consuming and expensive wet granulation technique was used.

U.S. Pat. No. 4,661,521 on direct tabletting acetaminophen composition to Salpekar et al, N-acetyl-p-aminophenol could only be directly compressed using additional steps such as slugging or roller compaction of the tabletting mix. Salpekar et al employed fluidized bed apparatus for thorough blending of N-acetyl-p-aminophenol with pregelatinized starch. High shear mixing is used to form a slurry which is dried and fluidized again before sizing to achieve the appropriate particle size.

Another limitation of direct compression as a method of tablet manufacturing is the potential size of the compressed tablets. If the amount of active ingredient is high, a pharmaceutical formulator may choose to wet granulate the active ingredient with other excipients to attain an acceptable sized tablet with the desired amount of acetaminophen. The amount of filler, binder or other excipients needed in wet granulation is less than that required for direct compression since the process of wet granulation contributes toward the desired physical properties of the tablet.

Hydroxypropyl methylcellulose has been utilized in the pharmaceutical industry as a direct compression excipient for solid dose forms. Hydroxypropyl methylcellulose is a processed cellulose and controls drug release from solid dosage forms.

Despite the advantages of the direct compression, such as reduced processing time and cost, wet granulation is widely used in the industry to prepare solid dosage forms. Wet granulation is often preferred over direct compression because wet granulation has a greater chance of overcoming any problems associated with the physical characteristics of various ingredients in the formulation. This provides material which has the required flow and cohesive properties necessary to obtain an acceptable solid dosage form.

The popularity of wet granulation compared to direct compression is based on at least three advantages. First, wet granulation provides the material to be compressed with better wetting properties, particularly in the case of hydrophobic drug substances. The addition of hydrophilic excipients makes the surface of the hydrophobic drug more hydrophilic, reducing disintegration and dissolution problems. Second, the content uniformity of the solid dosage form is generally improved with wet granulation because all of the granules usually contain the same amount of drug. Lastly, the segregation of drug(s) from excipients is avoided.

Segregation could be a potential problem with direct compression. The size and shape of particles comprising the granulate to be compressed are optimized through the wet granulation process. This is because when a dry solid is wet granulated the binder "glues" particles together, so that they agglomerate into spherical granules.

In spite of the advantages afforded by wet granulation, many manufacturers would welcome the opportunity to directly compress tablets containing high dose metformin HCl. There is a need in the industry for techniques and pharmaceutical excipients which will allow manufacturers to prepare high dose metformin HCl tablets by direct compression which will avoid the time and expense of wet granulation.

OBJECTS OF THE INVENTION

It is an object of the invention to provide a metformin HCl formulation in the form of a free-flowing, cohesive tableting powder, capable of being directly compressed into a tablet.

It is a further object of the invention to provide a compressed metformin HCl tablet in unit dosage form having an acceptable dissolution profile as well as acceptable degrees of hardness and resistance to chipping, as well as a short disintegration time.

It is a further object of the invention to provide a process for preparing a compressed metformin HCl tablet by direct compression in unit dosage form.

SUMMARY OF THE INVENTION

The present invention provides a direct tableting, free-flowing particulate metformin HCl formulation in the form of a tableting powder, capable of being directly compressed into a tablet having adequate hardness, rapid disintegration time, and an acceptable dissolution pattern. The formulation comprises the following:

(a) 70 to 79% by weight on a dry weight basis of metformin HCl having a particle size range of about 400 to 600 microns and a density range of 0.75 to 0.90 g/ml;

(b) 10 to 20% by weight on a dry weight basis of a pharmaceutically acceptable hydroxypropyl methylcellulose having a number average molecular weight of 80,000 to 90,000, a particle size range of about 400 to 600 microns and a density range of 0.25 to 0.70 g/ml as a diluent and binder;

(c) 0.1 to 15% by weight on a dry weight basis of a pharmaceutically acceptable hydroxypropyl cellulose having a number average molecular weight of 800,000 to 1,200,000, and a particle size range of about 177 to 590 microns as a diluent and binder;

(d) 5 to 15% by weight on a dry weight basis of a pharmaceutically acceptable polymerized povidone having a number average molecular weight of 300,000 to 1,000,000 as a binder capable of bonding the other ingredients in this composition under direct pressure into tablet form;

(e) 1 to 10% by weight on a dry weight basis of a pharmaceutically acceptable dibasic calcium phosphate in the form of spherically granulated particles having a particle size range of 400 to 450 microns, an angle of repose of 28 to 35 degrees, and a density range of 0.35 to 0.60 g/ml to improve flow and compression characteristics of the tableting powder;

(f) 1 to 10% by weight on a dry weight basis of microcrystalline cellulose, having a density range of 0.2 to 0.45 g/ml, which is compressible into a tablet;

(g) 0.1 to 2% by weight on a dry weight basis of colloidal silicon dioxide, having a density range of 0.029 to 0.040 g/ml as a glidant to improve flow characteristics of the tableting powder; and (h) 0.1 to 2% by weight on a dry weight basis of a pharmaceutically acceptable solid lubricant having a particle size of about 450 to 550 microns and a density of 1.00 to 1.80 g/ml to facilitate compression and ejection of tablets from a die cavity used in the tableting process.

The present invention further provides a compressed metformin HCl tablet in unit dosage form which comprises:

(a) 70 to 79% by weight on a dry weight basis of metformin HCl having a particle size range of about 400 to 600 microns and a density range of 0.75 to 0.90 g/ml;

(b) 10 to 20% by weight on a dry weight basis of a pharmaceutically acceptable hydroxypropyl methylcellulose as a diluent and binder having a number average molecular weight of 80,000 to 90,000, a particle size range of about 400 to 600 microns and a density range of 0.25 to 0.70 g/ml;

(c) 0.1 to 15% by weight on a dry weight basis of a pharmaceutically acceptable hydroxypropyl cellulose having a number average molecular weight of 800,000 to 1,200,00, and a particle size range of about 177 to 590 microns as a diluent and binder;

(d) 5 to 15% by weight on a dry weight basis of a pharmaceutically acceptable polymerized povidone having a number average molecular weight of 300,000 to 1,000,000, as a binder capable of bonding the other ingredients in this composition under direct pressure into tablet form;

(e) 1 to 10% by weight on a dry weight basis of a pharmaceutically acceptable dibasic calcium phosphate in the form of spherically granulated particles having a particle size range of 400 to 450 microns, an angle of repose of 28 to 35 degrees, and a density range of 0.35 to 0.60 g/ml to improve flow and compression characteristics of the tableting powder;

(f) 1 to 10% by weight on a dry weight basis of microcrystalline cellulose, having a density range of 0.2 to 0.45 g/ml, which is compressible into a tablet;

(g) 0.1 to 2% by weight on a dry weight basis of colloidal silicon dioxide, having a density range of 0.029 to 0.040 g/ml as a glidant to improve flow characteristics of the tableting powder; and (h) 0.1 to 2% by weight on a dry weight basis of a pharmaceutically acceptable solid lubricant having a particle size of about 450 to 550 microns and a density of 1.00 to 1.80 g/ml to facilitate compression and ejection of the tablets from a die cavity used in the tableting process.

The invention also provides a process for preparing a compressed metformin HCl tablet in unit dosage form which comprises:

(a) 70 to 79% by weight on a dry weight basis of metformin HCl having a particle size range of about 400 to 600 microns and a density range of 0.75 to 0.90 g/ml;

(b) 10 to 20% by weight on a dry weight basis of a pharmaceutically acceptable hydroxypropyl methylcellulose having a number average molecular weight of 80,000 to 90,000, a particle size range of about 400 to 600 microns and a density range of 0.25 to 0.70 g/ml as a diluent and binder;

(c) 0.1 to 15% by weight on a dry weight basis of a pharmaceutically acceptable hydroxypropyl cellulose having a number average molecular weight of 800,00 to 1,200,00, and a particle size range of about 177 to 590 microns as a diluent and binder;

(d) 5 to 15% by weight on a dry weight basis of a pharmaceutically acceptable polymerized povidone having a number average molecular weight of 300,000 to 1,000,000 as a binder capable of bonding the other ingredients in this composition under direct pressure into tablet form;

(e) 1 to 10% by weight on a dry weight basis of a pharmaceutically acceptable dibasic calcium phosphate in the form of spherically granulated particles having a particle size range of 400 to 450 microns, an angle of repose of 28 to 35 degrees, and a density range of 0.35 to 0.60 g/ml to improve flow and compression characteristics of the tableting powder;

(f) 1 to 10% by weight on a dry weight basis of microcrystalline cellulose, having a density range of 0.2 to 0.45 g/ml, which is compressible into a tablet;

(g) 0.1 to 2% by weight on a dry weight basis of colloidal silicon dioxide, having a density range of 0.029 to 0.040 g/ml as a glidant to improve flow characteristics of the tableting powder; and (h) 0.1 to 2% by weight on a dry weight basis of a pharmaceutically acceptable solid lubricant having a particle size of about 450 to 550 microns and a density of 1.00 to 1.80 g/ml to facilitate compression and ejection of the tablets from a die cavity used in the tableting process, which comprises the steps of:

(1) blending as a % by weight on a dry weight basis 70 to 79% of metformin HCl having a particle size range of about 400 to 600 microns and a density range of 0.75 to 0.90 g/ml, 10 to 20% of a pharmaceutically acceptable hydroxypropyl methylcellulose having a number average molecular weight of 80,000 to 90,000, a particle size range of about 400 to 600 microns and a density range of 0.25 to 0.70 g/ml as a diluent and binder, 0.1 to 15% of a pharmaceutically acceptable hydroxypropyl cellulose having a number average molecular weight of 800,000 to 1,200,000, and a particle size range of about 177 to 590 microns as a diluent and binder, 5 to 15% of a pharmaceutically acceptable polymerized povidone having a number average molecular weight of 300,000 to 1,000,000 as a binder capable of bonding the other ingredients in this composition under direct pressure into tablet form, 1 to 10% of a pharmaceutically acceptable dibasic calcium phosphate in the form of spherically granulated particles having a particle size range of 400 to 450 microns, an angle of repose of 28 to 35 degrees, and a density range of 0.35 to 0.60 g/ml to improve flow and compression characteristics of the tableting powder, 1 to 10% of microcrystalline cellulose, having a density range of 0.2 to 0.45 g/ml, which is compressible into a tablet, 0.1 to 2% of colloidal silicon dioxide, having a density range of 0.029 to 0.040 g/ml as a glidant to improve flow characteristics of the tableting powder, and 0.1 to 2% of a pharmaceutically acceptable solid lubricant having a particle size of about 450 to 550 microns and a density of 1.00 to 1.80 g/ml to facilitate compression and ejection of the tablets from a die cavity used in the tableting process, to form a metformin HCl formulation in the form of a tableting powder, capable of being directly compressed into a tablet; and (2) compressing the formulation prepared during step (1) to form the compressed metformin tablet in unit dosage form.

Salpekar et al patented direct compression of N-acetyl-p-aminophenol using additional steps such as slugging or roller compaction of the tableting mix. In compressing N-acetyl-p-aminophenol using direct compression, fluidized bed apparatus had been used for thorough blending with pregelatinized starch. Also Sheth et al in U.S. Pat. No. 3,671,633 patented direct compression of acetazolamide by first crystallizing acetazolamide from solution using acetazolamide seed crystals, and also employed granulation or slugging to obtain suitable sized granules prior to compression.

This present invention of direct compression of metformin HCl involves blending and compression. It does not involve previously used processes (for direct compression) such as granulation, slugging or roller compaction (chilsonation). The choice of grades of excipients took into consideration particle size maintained within a range that allows homogeneity of the powder mix and content uniformity of metformin HCl. It prevents segregation of powders in the hopper during direct compression. The advantages of using these excipients are that they impart compressibility, cohesiveness, and flowability of the powder blend. In addition, the use of direct compression provides competitive unit production cost, eliminates heat and moisture, allows for prime particle dissociation, physical stability, and ensures particle size uniformity.

DETAILED DESCRIPTION OF THE INVENTION

The N,N-dimethylimidodicarbonimidic diamide hydrochloride (metformin HCl) component, that may be 98.5–100% pure, of this invention is preferably provided as while crystalline powder. It has a particle size range of 400–600 microns and a density range of 0.75–0.90 g/ml. Metformin HCl is hygroscopic, freely soluble in water and inherently incompressible.

The use of 2-hydroxypropylmethylcellulose (hydroxypropyl methylcellulose) and hydroxypropyl cellulose in the formulation presents a unique quality of metformin HCl tablets in terms of the dissolution. Both polymers can form a dynamic hydrophilic matrix system that slows the release of the metformin HCl. They partially hydrate by wetting following tablet ingestion and form a gel layer. An initial burst of drug from the tablet layer is released. Water permeates into the tablet, increasing the thickness of the gel layer, and metformin HCl diffuses out of the gel layer.

The metformin HCl tablet becomes fully hydrated and gradually releases into an aqueous medium. Water continues to move towards the tablet core. Metformin HCl is released by diffusion from the gel layer and by exposure through tablet erosion. The high solubility of other excipients aids in hydrating the outer layer of the tablet to form a gel layer. The dissolution rate of metformin HCl is dependent on the rate of drug diffusion out of the wet gel and rate of tablet erosion.

For use in this invention, the particle size range of hydroxypropyl methylcellulose is from 400–600 microns, and a density range of 0.25–0.70 g/ml. Hydroxypropylcellulose has a particle size range of 177–590 microns. This profile contributes to consistent particle size of the final blend and eliminates problems of content uniformity. The high viscosity and density slow the release of metformin HCl from the tablets.

Hydroxypropyl methylcellulose is chemically substituted with 28–30% methoxyl and 7–12% hydroxypropoxyl groups. This chemical substitution allows for a faster hydration rate. Studies indicate that the faster hydrating polymers significantly control the release of drug. Among the grades of hydroxypropyl methylcellulose available, there is a significant difference in the rate at which polymers will hydrate. The grade of hydroxypropyl methylcellulose used contributes greatly to the rate of hydration of the tablets. In general, such an effective amount of hydroxypropyl methylcellulose is from 5 to 25% of the composition.

The composition also includes dibasic calcium phosphate anhydrous SG (spherically granulated), which provides a superior performance in direct compression due to its exceptional flow and compression characteristics. For use in this invention, dibasic calcium phosphate anhydrous SG should have a particle size range of 400 to 450 microns, (showing consistency with particle sizes of other ingredients), with an angle of repose of 28–35 degrees and density range of 0.35–0.60 g/ml.

The combination of dibasic calcium phosphate, anhydrous SG with other excipients provides significantly improved compressibility and flowability, compared to conventional anhydrous dibasic calcium phosphate and dibasic calcium phosphate dihydrates. The spherical nature and particle size assist in the compressibility of the tablet mix. This results in a mix with greatly reduced interparticle friction, leading to efficient blending and exceptional flow. This flowability reduces the variation in the tablet weight and hardness. Under direct compression, dibasic calcium phosphate anhydrous SG provides harder tablets than conventional excipients. In general, usage level is from 1 to 10% of the composition.

Microcrystalline cellulose is another excipient that may be used in the formulation. It is highly compressible and produces hard, strong tablets at a low machine pressure. This prevents chipping and capping of the metformin HCl tablets. Microcrystalline cellulose has a particle size range of 150–200 microns and a density range of 0.20–0.45 g/ml. It has inherent binding and superior tableting flow properties. It contributes to the lubrication of the powders in the die cavity and on the punch faces. In this way, it prevents adherence of tablets to the punches during compression.

In this invention, colloidal silicon dioxide with superior flow is ideally suited for use as a glidant. It improves the flow of powder blend in the hopper and into the die. Colloidal silicon dioxide has a density range of 0.029–0.040 g/ml. Generally, the usage level is from 0.1–2% of the formulation.

The lubricant component may be hydrophobic or hydrophilic. Examples of such lubricants include stearic acid, talc, and magnesium stearate. Magnesium stearate is preferable, and its addition as a lubricant is very important in our formulation. It reduces the friction between the die wall and tablet mix during the compression and ejection of metformin HCl tablets. It helps prevent adhesion of tablets to the punches and dies. Magnesium stearate also aids in the flow of the powder in the hopper and into the die. It has a particle size range of 450–550 microns and a density range of 1.00–1.80 g/ml. It is stable and does not polymerize within the tableting mix. The level of 0.1–2.0% magnesium stearate is used in the formulation.

Optionally, the composition may include specially designed, pharmaceutically acceptable and compressible anhydrous lactose, having a particle size of 70–110 microns and a density of 1.0–2.0 g/ml. Lactose is used as a diluent. It is recommended that lactose be combined with microcrystalline cellulose or calcium phosphate. In general, an effective amount of optimal diluent is from 1 to 10%, preferably 5% to 10%.

The particle size ranges of the metformin HCl as well as of the excipients are considered critical to the success of the invention. These particle size ranges are necessary to obtain a free-flowing, cohesive tableting powder, capable of direct compression into a tablet.

A preferred composition of the ingredients and their respective amounts as percent of the composition at the time of invention are indicated in the table below. Such composition of the formula can be repeatedly compressed into tablets using direct compression having the desired degree of hardness, resistance to chipping, capping and lamination. In addition, the tablet has an acceptable dissolution profile. The composition of this invention is made by the direct compression method, which include blending and compression. The proportions of metformin HCl and excipients are indicated below:

| COMPONENTS | APPROXIMATE AMOUNT (%0-./) |
|---|---|
| N,N-dimethylimidodicarbonimidic diamide hydrochloride (Metformin HCl) | 70–79 |
| 2-hydroxypropylmethylcellulose | 10–20 |
| Hydroxypropyl cellulose | 1–15 |
| 1-vinyl-2-pyrrolidinone (Povidone) | 5–15 |
| Microcrystalline cellulose | 1–10 |
| Lactose | 1–10 |
| Dibasic calcium phosphate | 1–10 |
| Colloidal silicon dioxide | 0.1–2 |
| Magnesium Stearate | 0.1–2 |

The following examples are merely illustrative of the present invention and they should not be considered as limiting the scope of the invention in any way, as these examples and other equivalents thereof will become apparent to those versed in the art in the light of the present disclosure, and the accompanying claims. Example 1 represents the basic direct compression formulation of metformin HCl 500 mg tablets.

EXAMPLE 1

| Ingredient | Weight (mg) per tablet |
|---|---|
| Metformin HCl | 500.00 |
| Microcrystalline cellulose | 36.85 |
| Hydroxypropyl methylcellulose | 77.90 |
| Povidone | 26.80 |
| Colloidal silicon dioxide | 3.25 |
| Magnesium stearate | 5.20 |
| Total | 650.00 |

The ingredients were weighed and blended in Patterson Kelly "V" blender at a speed of 27 rpm for 5 minutes. Subsequently, magnesium stearate and colloidal silicon dioxide were screened through a 30 mesh screen, added to the blender, and mixed for 5 minutes. The resulting final blend was compressed into tablets using a rotary tablet press in a controlled environment. Tablets were compressed at a compression weight of 650 mg using round, concave punches.

The manufacturing method of Example 1 was repeated in Examples 2 to 10 except that the basic formulation in Example 1 was modified. The total weight of each compressed tablet is indicated in the examples below.

EXAMPLE 2

| Ingredient | Weight (mg) per tablet |
|---|---|
| Metformin HCl | 500.00 |
| Microcrystalline cellulose | 36.85 |
| Hydroxypropyl methylcellulose | 80.00 |
| Povidone | 46.90 |

EXAMPLE 2

| Ingredient | Weight (mg) per tablet |
|---|---|
| Colloidal silicon dioxide | 3.25 |
| Magnesium stearate | 5.20 |
| Total | 672.20 |

EXAMPLE 3

| Ingredient | Weight (mg) per tablet |
|---|---|
| Metformin HCl | 500.00 |
| Microcrystalline cellulose | 36.85 |
| Hydroxypropyl methycellulose | 81.60 |
| Povidone | 54.40 |
| Colloidal silicon dioxide | 3.25 |
| Magnesium stearate | 5.20 |
| Total | 681.30 |

EXAMPLE 4

| Ingredient | Weight (mg) per tablet |
|---|---|
| Metformin HCl | 500.00 |
| Microcrystalline cellulose | 27.00 |
| Hydroxypropyl methycellulose | 76.60 |
| Povidone | 53.00 |
| Colloidal silicon dioxide | 3.25 |
| Magnesium stearate | 5.20 |
| Total | 655.05 |

EXAMPLE 5

| Ingredient | Weight (mg) per tablet |
|---|---|
| Metformin HCl | 500.00 |
| Microcrystalline cellulose | 36.85 |
| Hydroxypropyl methycellulose | 97.90 |
| Povidone | 26.80 |
| Colloidal silicon dioxide | 3.25 |
| Magnesium stearate | 5.20 |
| Total | 670.00 |

EXAMPLE 6

| Ingredient | Weight (mg) per tablet |
|---|---|
| Metformin HCl | 500.00 |
| Microcrystalline cellulose | 36.00 |
| Hydroxypropyl methycellulose | 63.00 |
| Povidone | 26.80 |
| Magnesium stearate | 5.20 |
| Total | 631.00 |

EXAMPLE 7

| Ingredient | Weight (mg) per tablet |
|---|---|
| Metformin HCl | 500.00 |
| Silicified microcrystalline cellulose | 46.00 |
| Hydroxypropyl methycellulose | 75.80 |
| Magnesium stearate | 5.20 |
| Total | 627.00 |

EXAMPLE 8

| Ingredient | Weight (mg) per tablet |
|---|---|
| Metformin HCl | 500.00 |
| Silicified microcrystalline cellulose | 36.85 |
| Polyvinylpyrrolidone | 26.80 |
| Hydroxypropyl methycellulose | 100.50 |
| Colloidal silicon dioxide | 3.25 |
| Magnesium stearate | 5.20 |
| Total | 672.60 |

EXAMPLE 9

| Ingredient | Weight (mg) per tablet |
|---|---|
| Metformin HCl | 500.00 |
| Lactose | 33.50 |
| Polyvinylpyrrolidone | 40.20 |
| Hydroxypropyl methycellulose | 100.50 |
| Colloidal silicon dioxide | 3.25 |
| Magnesium stearate | 5.20 |
| Total | 682.65 |

EXAMPLE 6

| Ingredient | Weight (mg) per tablet |
|---|---|
| Metformin HCl | 500.00 |
| Maltose | 46.00 |
| Dibasic calcium phosphate | 45.00 |
| Mannitol | 43.00 |
| Colloidal silicon dioxide | 3.25 |
| Magnesium stearate | 5.20 |
| Total | 642.45 |

What is claimed is:

1. A metformin HCl formulation in the form of a tableting powder, capable of being directly compressed into a tablet, which comprises:
   (a) 70 to 79% by weight on a dry weight basis of metformin HCl having a particle size range of about 400 to 600 microns and a density range of 0.75 to 0.90 g/ml;
   (b) 10 to 20% by weight on a dry weight basis of a pharmaceutically acceptable hydroxypropyl methylcellulose having a number average molecular weight of 80,000 to 90,000, a particle size range of about 400 to 600 microns and a density range of 0.25 to 0.70 g/ml as a diluent and binder;

(c) 0.1 to 15% by weight on a dry weight basis of a pharmaceutically acceptable hydroxypropyl cellulose having a number average molecular weight of 800,000 to 1,200,000 and a particle size range of about 177 to 590 microns as a diluent and binder;

(d) 5 to 15% by weight on a dry weight basis of a pharmaceutically acceptable polymerized povidone having a number average molecular weight of 300,000 to 1,000,000 as a binder capable of bonding the other ingredients in this composition under direct pressure into tablet form;

(e) 1 to 10% by weight on a dry weight basis of a pharmaceutically acceptable dibasic calcium phosphate in the form of spherically granulated particles having a particle size range of 400 to 450 microns, an angle of repose of 28 to 35 degrees, and a density range of 0.35 to 0.60 g/ml to improve flow and compression characteristics of the tableting powder;

(f) 1 to 10% by weight on a dry weight basis of microcrystalline cellulose, having a density range of 0.2 to 0.45 g/ml, which is compressible into a tablet;

(g) 0.1 to 2% by weight on a dry weight basis of colloidal silicon dioxide, having a density range of 0.029 to 0.040 g/ml as a glidant to improve flow characteristics of the tableting powder; and (h) 0.1 to 2% by weight on a dry weight basis of a pharmaceutically acceptable solid lubricant having a particle size of about 450 to 550 microns and a density of 1.00 to 1.80 g/ml to facilitate compression and ejection of tablets from a die cavity used in the tableting process.

2. The metformin HCl formulation defined in claim 1 wherein the solid pharmaceutically acceptable lubricant is magnesium stearate present in an amount of 0.1 to 1% by weight.

3. The metformin HCl formulation defined in claim 1 wherein about 15% on a dry weight basis of the hydroxypropyl methylcellulose is present and about 1% by weight on a dry weight basis of the pharmaceutically acceptable solid lubricant is present.

4. The metformin HCl formulation defined in claim 1 wherein about 10% on a dry weight basis of the hydroxypropyl methylcellulose is present, about 1% by weight on a dry weight basis of the pharmaceutically acceptable solid lubricant is present, and about 10% by weight on a dry weight basis of the povidone is present.

5. The metformin HCl formulation defined in claim 1 wherein the hydroxypropyl methylcellulose contains about 10 to 20% by weight of solids.

6. The metformin HCl formulation defined in claim 1 wherein all ingredients except for the pharmaceutically acceptable solid lubricant are present as a blend and then the lubricant is added to the blend.

7. The metformin HCl formulation defined in claim 1 which further comprises as a diluent 1 to 10% by weight on a dry weight basis of pharmaceutically acceptable, compressible anhydrous lactose having a particle size of 70 to 110 microns and a density of 1.0 to 2.0 g/ml.

8. A compressed metformin HCl tablet 500 to 850 mg in unit dosage form which comprises:

(a) 70 to 79% by weight on a dry weight basis of metformin HCl having a particle size range of about 400 to 600 microns and a density range of 0.75 to 0.90 g/ml;

(b) 10 to 20% by weight on a dry weight basis of a pharmaceutically acceptable hydroxypropyl methylcellulose having a number average molecular weight of 80,000 to 90,000, a particle size range of about 400 to 600 microns and a density range of 0.25 to 0.70 g/ml as a diluent and binder;

(c) 0.1 to 15% by weight on a dry weight basis of a pharmaceutically acceptable hydroxypropyl cellulose having a number average molecular weight of 800,000 to 1,200,000, and a particle size range of about 177 to 590 microns as a diluent and binder;

(d) 5 to 15% by weight on a dry weight basis of a pharmaceutically acceptable polymerized povidone having a number average molecular weight of 300,000 to 1,000,000, as a binder capable of bonding the other ingredients in this composition under direct pressure into tablet form;

(e) 1 to 10% by weight on a dry weight basis of a pharmaceutically acceptable dibasic calcium phosphate in the form of spherically granulated particles having a particle size range of 400 to 450 microns, an angle of repose of 28 to 35 degrees, and a density range of 0.35 to 0.60 g/ml to improve flow and compression characteristics of the tableting powder;

(f) 1 to 10% by weight on a dry weight basis of microcrystalline cellulose, having a density range of 0.2 to 0.45 g/ml, which is compressible into a tablet;

(g) 0.1 to 2% by weight on a dry weight basis of colloidal silicon dioxide, having a density range of 0.029 to 0.040 g/ml as a glidant to improve flow characteristics of the tableting powder; and (h) 0.1 to 2% by weight on a dry weight basis of a pharmaceutically acceptable solid lubricant having a particle size of about 450 to 550 microns and a density of 1.00 to 1.80 g/ml to facilitate compression and ejection of the tablets from a die cavity used in the tableting process.

9. A process for preparing a compressed metformin HCl tablet in unit dosage form which comprises:

(a) 70 to 79% by weight on a dry weight basis of metformin HCl having a particle size range of about 400 to 600 microns and a density range of 0.75 to 0.90 g/ml;

(b) 10 to 20% by weight on a dry weight basis of a pharmaceutically acceptable hydroxypropyl methylcellulose having a number average molecular weight of 80,000 to 90,000, a particle size range of about 400 to 600 microns and a density range of 0.25 to 0.70 g/ml as a diluent and binder;

(c) 0.1 to 15% by weight on a dry weight basis of a pharmaceutically acceptable hydroxypropyl cellulose having a number average molecular weight 800,000 to 1,200,000, and a particle size range of about 177 to 590 microns as a diluent and binder;

(d) 5 to 15% by weight on a dry weight basis of a pharmaceutically acceptable polymerized povidone having a number average) molecular weight of 300,000 to 1,000,000 as a binder capable of bonding the other ingredients in this composition under direct pressure into tablet form;

(e) 1 to 10% by weight on a dry weight basis of a pharmaceutically acceptable dibasic calcium phosphate in the form of spherically granulated particles having a particle size range of 400 to 450 microns, an angle of repose of 28 to 35 degrees, and a density range of 0.35 to 0.60 g/ml to improve flow and compression characteristics of the tableting powder;

(f) 1 to 10% by weight on a dry weight basis of microcrystalline cellulose, having a density range of 0.2 to 0.45 g/ml, which is compressible into a tablet;

(g) 0.1 to 2% by weight on a dry weight basis of colloidal silicon dioxide, having a density range of 0.029 to 0.040 g/ml as a glidant to improve flow characteristics of the tableting powder; and (h) 0.1 to 2% by weight on a dry weight basis of a pharmaceutically acceptable solid lubricant having a particle size of about 450 to 550 microns and a density of 1.00 to 1.80 g/ml to facilitate compression and ejection of the tablets from a die cavity used in the tableting process, which comprises the steps of:

(1) blending as a % by weight on a dry weight basis 70 to 79% of metformin HCl having a particle size range of about 400 to 600 microns and a density range of 0.75 to 0.90 g/ml, 10 to 20% of a pharmaceutically acceptable hydroxypropyl methylcellulose having a number average molecular weight of 80,000 to 90,000, a particle size range of about 400 to 600 microns and a density range of 0.25 to 0.70 g/ml as a diluent and binder, 0.1 to 15% of a pharmaceutically acceptable hydroxypropyl cellulose having a number average molecular weight of 800,000 to 1,200,000, a particle size range of about 177 to 590 microns as a diluent and binder, 5 to 15% of a pharmaceutically acceptable polymerized povidone having a number average molecular weight of 300,000 to 1,000,000 as a binder capable of bonding the other ingredients in this composition under direct pressure into tablet form, 1 to 10% of a pharmaceutically acceptable dibasic calcium phosphate in the form of spherically granulated particles having a particle size range of 400 to 450 microns, an angle of repose of 28 to 35 degrees, and a density range of 0.35 to 0.60 g/ml to improve flow and compression characteristics of the tableting powder, 1 to 10% of microcrystalline cellulose, having a density range of 0.2 to 0.45 g/ml, which is compressible into a tablet, 0.1 to 2% of colloidal silicon dioxide, having a density range of 0.029 to 0.040 g/ml as a glidant to improve flow characteristics of the tableting powder, and 0.1 to 2% of a pharmaceutically acceptable solid lubricant having a particle size of about 450 to 550 microns and a density of 1.00 to 1.80 g/ml to facilitate compression and ejection of the tablets from a die cavity used in the tableting process, to form a metformin HCl formulation in the form of a tableting powder, capable of being directly compressed into a tablet; and (2) compressing the formulation prepared during step (1) to form the compressed metformin HCl tablet in unit dosage form.

\* \* \* \* \*